United States Patent [19]

McCandlish et al.

[11] 4,345,038
[45] Aug. 17, 1982

[54] CO HYDROGENATION PROCESS USING STEAM AND MOLYBDENUM OXYCARBONITRIDE CATALYST

[75] Inventors: Larry E. McCandlish, Highland Park; Franklin J. Wright, Watchung; Edwin L. Kugler, Summit, all of N.J.

[73] Assignee: Exxon Research & Engineering Co., Florham Park, N.J.

[21] Appl. No.: 304,980

[22] Filed: Sep. 23, 1981

Related U.S. Application Data

[63] Continuation-in-part of Ser. No. 216,139, Dec. 15, 1980, abandoned.

[51] Int. Cl.$^3$ ............................................. C07C 1/10
[52] U.S. Cl. .................................. 518/711; 518/714; 585/733
[58] Field of Search ................. 518/711, 714; 585/733

[56] References Cited

U.S. PATENT DOCUMENTS

| | | |
|---|---|---|
| 3,492,100 | 1/1970 | Roubin et al. . |
| 3,872,136 | 3/1975 | Middelboek . |
| 4,128,621 | 12/1978 | Homeier . |
| 4,163,775 | 8/1979 | Foster et al. . |
| 4,239,536 | 12/1980 | Yamamoto et al. . |

FOREIGN PATENT DOCUMENTS

| | | |
|---|---|---|
| 53-10692 | 1/1978 | Japan . |
| 4134719 | 10/1979 | Japan . |
| 5031517 | 3/1980 | Japan . |

OTHER PUBLICATIONS

Bureau of Mines Report of Investigation No. 6974 (Jul. 1967) by J. F. Schultz, F. S. Karn and R. B. Anderson.
Nature pp. 1327–1328 (Jun. 1964).
Le Clercq et al., "Preparation of Catalysts II", Elsevier Sci. Publ. 3, 627 (1979).
Boudart et al., "Seventh International Congress on Catalysis", Tokyo, Jul. 3–4 (1980), Preprint A–40.

*Primary Examiner*—Howard T. Mars
*Attorney, Agent, or Firm*—Robert J. North

[57] ABSTRACT

A process for synthesizing light paraffinic hydrocarbons, preferably $C_1$–$C_3$ in carbon number, from CO and steam is described utilizing novel molybdenum oxycarbonitride catalyst.

8 Claims, No Drawings

CO HYDROGENATION PROCESS USING STEAM AND MOLYBDENUM OXYCARBONITRIDE CATALYST

CROSS REFERENCE TO RELATED APPLICATIONS

This is a continuation-in-part application of U.S. Ser. No. 216,139, filed Dec. 15, 1980 now abandoned.

BACKGROUND OF THE INVENTION

1. Field of the Invention

This invention relates to a process for synthesizing light paraffinic hydrocarbons, preferably $C_1$-$C_3$ in carbon number, from CO and steam by contacting mixtures thereof with molybdenum oxycarbonitride catalyst.

2. Brief Description of the Prior Art

CO hydrogenation with steam is well known in the art and is generally referred to as the Kolbel-Engelhardt process. In the process, mixtures of CO and steam are usually contacted with an iron-based catalyst at high temperature and pressure resulting in a board hydrocarbon distribution from $C_1$ to $C_{20}$ carbon number, including gaseous, liquid and solid products, and also including high molecular weight waxes.

New catalysts for the process are constantly being searched for and evaluated in order to improve the selectivity of the process for producing a particularly desired range of hydrocarbons or to stabilize the selectivity of the process over a broad range of operating parameters.

The novel composition, molybdenum oxycarbonitride, is a subject of co-pending application, Ser. No. 209,998 in which the properties of this new material, physical structure, distinguishing physical characteristics, methods of preparation, and its use as an abrasive, are thoroughly described and is hereby incorporated by reference for that purpose. However, the reference does not specifically suggest or describe any catalyst properties of the composition.

SUMMARY OF THE INVENTION

We have unexpectedly found that molybdenum oxycarbonitride, a novel composition, is an excellent catalyst for use in CO hydrogenation utilizing steam for selectively producing light paraffinic hydrocarbons and particularly $C_1$-$C_3$ parraffins and mixtures thereof. This is especially surprising since the composition could be viewed as being particularly reactive with water. Further, we have found that no significant carbon deposition occurs on the catalyst during a typical CO hydrogenation with steam.

In accordance with this invention, there is provided a process for preparing light paraffinic hydrocarbons including linear and branched $C_1$-$C_{10}$ carbon chain numbers, comprising contacting a gaseous mixture of CO and steam in a CO/steam volume ratio of 10:1 to 1:10, respectively, with a catalyst comprised of molybdenum oxycarbonitride, at a temperature in the range of about 100° to 600° C., a pressure of about 0.1 to 100 MPa, and a space velocity of about 100 to 50,000 v/v/hr., and recovering product paraffinic hydrocarbons. A preferred embodiment is where the product paraffinic hydrocarbons are mainly $C_1$-$C_3$ in carbon number.

DESCRIPTION OF THE INVENTION AND PREFERRED EMBODIMENTS

The molybdenum oxycarbonitride composition useful as a catalyst in the subject process is thoroughly described in the above-identified reference and preferably has a particle size less than 100 Å, as evidenced by a measured surface area of about 10 to 160 m²/gram (as measured by the well-known BET argon method and X-ray diffraction line broadening). However, molybdenum oxycarbonitride having larger and smaller surface areas than that described above, are also applicable in the subject process.

Generally, the catalyst is initially used in the passivated form, which is relatively stable, to avoid decomposition. The catalyst is then generally heat-treated in a reducing atmosphere to generate the reduced catalyst form prior to reaction.

The above-identified reference readily discloses a general procedure for producing the passivated form of molybdenum oxycarbonitride.

The empirical formula of the molybdenum oxycarbonitride is $MoO_aC_bN_c$, wherein a, b and c are non-zero decimal values and wherein the sum of a+b+c is less than or equal to about one. A preferred composition for use in the process is: $MoO_{0.41}C_{0.31}N_{0.33}$, produced, for example, from the thermal decomposition of ethylenediammonium molybdate at about 650° C. under a helium atmosphere.

The catalyst composition also can be unsupported or supported on conventional materials which are inert under the process conditions. Representative examples of suitable supports are alumina, silica, titania and the like. If supported, the catalyst support can be present in conventional amounts.

The process is conducted by contacting a mixture of carbon monoxide and steam with the above-described catalyst in a conventional reactor. Representative types of reactors and apparatus that can be employed are glass and stainless steel reactors that are vertical, horizontal or down-flow types which utilize the ctalyst as a fixed bed, fluid bed, slurry and the like.

The catalyst is generally pretreated at an elevated temperature in a reducing atmosphere for a period of time prior to the process. The temperature, atmosphere and time required are conventional in the art. A set of conditions which was found to be effective was pretreatment at 450° C. in a hydrogen atmosphere, at a space velocity of about 10,000 v/v/hr. for a time of about 2 hours. Other sets of conditions will be obvious to one skilled in the art.

The gaseous mixture of CO and steam is in a CO/steam volume ratio of 10:1 to 1:10, respectively, and preferably in a 1:3 to 3:1 ratio.

The CO used in the process can be commercially available of high purity and can contain small amounts of other gases which are inert under the reaction conditions such as nitrogen which can also be used as a carrier gas.

Steam for use in the process can be generated, for example, by saturating the CO feedstream with a conventional steam saturator.

The temperature of the process is conducted in the range of about 100° to 600° C., and preferably about 225°–450° C.

The pressure of the CO/steam feedstream in the process is carried out in the region of about 0.1 to 100 MPa and preferably about 0.1 to 3.0 MPa (1 atmosphere being equivalent to 0.1 MPa).

The space velocity of the CO/steam feedstream in the process is carried out in the range of 100 to 50,000 v/v/hr. and preferably about 100 to 2500 v/v/hr.

Product hydrocarbons are collected, separated and purified by conventional methods in the art.

The product paraffinic hydrocarbons include linear and branched $C_1$-$C_{10}$ hydrocarbons, preferably linear and include methane, ethane, propane, butane, pentane, hexane, heptane, octane, nonane, decane, isooctane, neodecane, isopentane, neopentane and the like. Preferably, $C_1$-$C_3$ hydrocarbons including methane, ethane, propane, and mixtures thereof, are preferred products in the process.

Percent CO conversions can vary in the process, depending upon the specific conditions employed, and can be in the range of about 30-80% and higher.

The following example is illustrative of the best mode of carrying out the invention as contemplated by us and should not be construed as being a limitation on the scope and spirit of the instant invention.

EXAMPLE

Five (5) cc of passivated molybdenum oxycarbonitride (prepared by the thermal decomposition of ethylenediammonium molybdate at 450° C. and having a BET argon surface area of about 100 m²/g were placed into a 1 cm. diameter stainless steel down-flow reactor. A thermocouple was placed into the center of the catalyst bed. The catalyst was pretreated in situ by passing a stream of hydrogen over the catalyst at 1 atmosphere, a space velocity of 480 v/v/hr. and a temperature of 400° C. for 78 hours. The temperature was then reduced to 300° C. and the pressure increased to 120 psia (about 0.8 MPa). The hydrogen feed was replaced by a mixture of 3:1 parts by volume of CO/steam and a small amount of nitrogen as an internal standard. The steam was generated by saturating a stream of carbon monoxide by bubbling through a saturator containing distilled deionized water at 121° C. at which the vapor pressure of water was 30 psi. Feedstream lines to the reactor were maintained above 121° C. to prevent condensation. The composition of the effluent gases was monitored for a period of 7 hours during the run which was conducted at 300° C., 120 psia (about 0.8 MPa), a space velocity of 400 v/v/hr., and a feed composition of 100 CO:33 $H_2O$(steam):2.04 $N_2$. The monitoring process was conducted by passing the reaction mixture through a cold trap maintained at $-1°$ C. The non-condensed gases were analyzed by on-stream gas chromatography versus known standards. Results of the monitoring revealed:

| CO conversion | 46.9% |
|---|---|
| Gaseous Products | |
| Methane | 21.35 g/NM³ of CO fed |
| Ethane | 13.24 g/NM³ of CO fed |
| Propane | 15.29 g/NM³ of CO fed |
| Butane | 8.94 g/NM³ of CO fed |
| Pentane | 5.37 g/NM³ of CO fed |
| Hexane | 4.81 g/NM³ of CO fed |
| Carbon Dioxide | 716.9 g/NM³ of CO fed |
| Hydrogen | 9.45 g/NM³ of CO fed |

No carbon deposition on the catalyst was observed. The weight of the recovered catalyst was substantially the same as the starting catalyst.

What is claimed is:

1. A process for preparing paraffinic hydrocarbons including linear and branched $C_1$-$C_{10}$ carbon chain number comprising contacting a gaseous mixture of CO and steam in a CO/steam volume ratio of 10:1 to 1:10, respectively, with a catalyst comprised of molybdenum oxycarbonitride, at a temperature in the range of about 100° to 600° C., a pressure of about 0.1 to 100 MPa, and a space velocity of about 100 to 50,000 v/v/hr., and recovering product paraffinic hydrocarbons.

2. The process of claim 1 wherein said molybdenum oxycarbonitride is of the formula: $MoO_aC_bN_c$, wherein, a, b and c are non-zero decimal values and wherein the sum of $a+b+c$ is less than or equal to about one.

3. The process of claim 1 wherein said molybdenum oxycarbonitride possesses a measured BET argon surface area of about 10 to 160 m²/g.

4. The process of claim 1 wherein said temperature is about 225° to 450° C.

5. The process of claim 1 wherein said pressure is about 0.1 to 3.0 MPa.

6. The process of claim 1 wherein the space velocity is about 100 to 2500 v/v/hr.

7. The process of claim 1 wherein said CO/steam volume ratio is about 1:3 to 3:1.

8. The process of claim 1 wherein said product paraffinic hydrocarbons mainly comprise methane, ethane, propane, or mixtures thereof.

* * * * *